United States Patent [19]
Thompson et al.

[11] Patent Number: 5,955,492
[45] Date of Patent: Sep. 21, 1999

[54] CARBOXYLIC ACID INDOLE INHIBITORS OF CHEMOKINES

[75] Inventors: Scott K. Thompson, Phoenixville; Stacie M. Halbert, Harleysville; Katherine L. Widdowson, King of Prussia, all of Pa.

[73] Assignee: SmithKline Beecham Corporation, Philadelphia, Pa.

[21] Appl. No.: 09/155,220

[22] PCT Filed: Mar. 27, 1997

[86] PCT No.: PCT/US97/04938

§ 371 Date: Sep. 24, 1998

§ 102(e) Date: Sep. 24, 1998

[87] PCT Pub. No.: WO97/35572

PCT Pub. Date: Oct. 2, 1997

Related U.S. Application Data

[60] Provisional application No. 60/014,257, Mar. 28, 1996.

[51] Int. Cl.$^6$ .................. A61K 31/405; C07C 62/36; C07D 209/18; C07D 405/06

[52] U.S. Cl. .................. 514/419; 514/382; 514/784; 514/826; 514/863; 548/250; 548/252; 548/254; 548/490; 548/491; 548/494; 549/440; 562/405; 562/466; 562/468

[58] Field of Search .................. 514/419, 784; 548/490, 491, 494

[56] References Cited

U.S. PATENT DOCUMENTS

| | | | |
|---|---|---|---|
| 4,148,895 | 4/1979 | Lattrell et al. | 424/248.54 |
| 5,399,699 | 3/1995 | Kolasa et al. | 546/174 |
| 5,482,960 | 1/1996 | Berryman et al. | 514/414 |

FOREIGN PATENT DOCUMENTS

WO9618393  6/1996  WIPO.

*Primary Examiner*—Johann Richter
*Assistant Examiner*—Jane C. Oswecki
*Attorney, Agent, or Firm*—Dara L. Dinner; Stephen Venetianer; Charles M. Kinzig

[57] ABSTRACT

This invention relates to novel carboxylic acid indole compounds and compositions for use in the treatment of disease states mediated by the chemokine, Interleukin-8 (IL-8).

13 Claims, No Drawings

CARBOXYLIC ACID INDOLE INHIBITORS OF CHEMOKINES

This application is a 371 of PCT/US97/04938 filed Mar. 27, 1997 and claims the benefit of Provisional Application No. 60/014,257 filed Mar. 28, 1996.

FIELD OF THE INVENTION

This invention relates to a novel group of carboxylic acid indole compounds, processes for the preparation thereof, the use thereof in treating IL-8, GROα, GROβ, GROγ and NAP-2 mediated diseases and pharmaceutical compositions for use in such therapy.

BACKGROUND OF THE INVENTION

Many different names have been applied to Interleukin-8 (IL-8), such as neutrophil attractant/activation protein-1 (NAP-1), monocyte derived neutrophil chemotactic factor (MDNCF), neutrophil activating factor (NAF), and T-cell lymphocyte chemotactic factor. Interleukin-8 is a chemoattractant for neutrophils, basophils, and a subset of T-cells. It is produced by a majority of nucleated cells including macrophages, fibroblasts, endothelial and epithelial cells exposed to TNF, IL-1α, IL-1β or LPS, and by neutrophils themselves when exposed to LPS or chemotactic factors such as FMLP. M. Baggiolini et al, *J. Clin. Invest.* 84, 1045 (1989); J. Schroder et al, *J. Immunol.* 139, 3474 (1987) and *J. Immunol.* 144, 2223 (1990); Strieter, et al, *Science* 243, 1467 (1989) and *J. Biol. Chem.* 264, 10621 (1989); Cassatella et al, *J. Immunol.* 148, 3216 (1992).

Groα, GROβ, GROγ and NAP-2 also belong to the chemokine α family. Like IL-8 these chemokines have also been referred to by different names. For instance GROα,β, γ have been referred to as MGSAα, β, and γ respectively (Melanoma Growth Stimulating Activity), see Richmond et al, J. Cell Physiology 129, 375 (1986) and Chang et al, *J. Immunol* 148, 451 (1992). All of the chemokines of the α-family which possess the ELR motif directly preceding the CXC motif bind to the IL-8 B receptor.

IL-8, Groα, GROβ, GROγ, NAP-2 and ENA-78 stimulate a number of functions in vitro. They have all been shown to have chemoattractant properties for neutrophils, while IL-8 and GROα have demonstrated T-lymphocytes, and basophiles chemotactic activity. In addition IL-8 can induce histamine release from basophils from both normal and atopic individuals GRO-α and IL-8 can in addition, induce lysozomal enzyme release and respiratory burst from neutrophils. IL-8 has also been shown to increase the surface expression of Mac-1 (CD11b/CD18) on neutrophils without de novo protein synthesis. This may contribute to increased adhesion of the neutrophils to vascular endothelial cells. Many known diseases are characterized by massive neutrophil infiltration. As IL-8, Groα, GROβ, GROγ and NAP-2 promote the accumulation and activation of neutrophils, these chemokines have been implicated in a wide range of acute and chronic inflammatory disorders including psoriasis and rheumatoid arthritis, Baggiolini et al, *FEBS Lett.* 307, 97 (1992); Miller et al, *Crit. Rev. Immunol.* 12, 17 (1992); Oppenheim et al, *Annu. Rev. Immunol.* 9, 617 (1991); Seitz et al., *J. Clin. Invest.* 87, 463 (1991); Miller et al., *Am. Rev. Respir. Dis.* 146, 427 (1992); Donnely et al., *Lancet* 341, 643 (1993). In addition the ELR chemokines (those containing the amino acids ELR motif just prior to the CXC motif) have also been implicated in angiostasis. Strieter et al, *Science* 258, 1798 (1992).

In vitro, IL-8, Groα, GROβ, GROγ and NAP-2 induce neutrophil shape change, chemotaxis, granule release, and respiratory burst, by binding to and activating receptors of the seven-transmembrane, G-protein-linked family, in particular by binding to IL-8 receptors, most notably the B-receptor. Thomas et al., *J. Biol. Chem.* 266, 14839 (1991); and Holmes et al., *Science* 253, 1278 (1991). The development of non-peptide small molecule antagonists for members of this receptor family has precedent. For a review see R. Freidinger in: *Progress in Drug Research*, Vol. 40, pp. 33–98, Birkhauser Verlag, Basel 1993. Hence, the IL-8 receptor represents a promising target for the development of novel anti-inflammatory agents.

Two high affinity human IL-8 receptors (77% homology) have been characterized: IL-8Rα, which binds only IL-8 with high affinity, and IL-8Rβ, which has high affinity for IL-8 as well as for GRO-α, GROβ, GROγ and NAP-2. See Holmes et al., supra; Murphy et al., *Science* 253, 1280 (1991); Lee et al.,*J. Biol. Chem.* 267, 16283 (1992); LaRosa et al., *J. Biol. Chem.* 267, 25402 (1992); and Gayle et al., *J. Biol. Chem.* 268, 7283 (1993).

There remains a need for treatment, in this field, for compounds which are capable of binding to the IL-8 α or β receptor. Therefore, conditions associated with an increase in IL-8 production (which is responsible for chemotaxis of neutrophil and T-cells subsets into the inflammatory site) would benefit by compounds which are inhibitors of IL-8 receptor binding.

SUMMARY OF THE INVENTION

This invention relates to the novel compounds of Formula (I) and pharmaceutical compositions comprising a compound of Formula (I) and a pharmaceutically acceptable diluent or carrier.

This invention provides for a method of treating a chemokine mediated disease, wherein the chemokine is one which binds to an IL-8 α or β receptor and which method comprises administering an effective amount of a compound of Formula (I) or a pharmaceutically acceptable salt thereof. In particular the chemokine is IL-8.

This invention also relates to a method of inhibiting the binding of IL-8 to its receptors in a mammal in need thereof which comprises administering to said mammal an effective amount of a compound of Formula (I).

Compounds of Formula (I) useful in the present methods are represented by the structure:

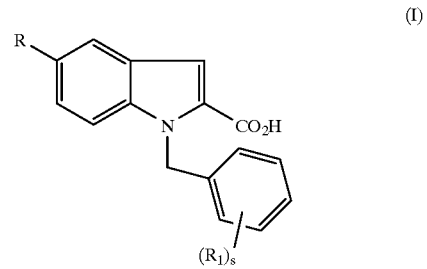

(I)

wherein
R is or X—(CH$_2$)$_n$—R$_6$;
X is oxygen or —C(O)—NH—;
R$_6$ is an optionally substituted C$_{3-7}$ cycloalkyl, optionally substituted C$_{3-7}$cycloalkenyl, or an optionally substituted aryl;
n is 0 or an integer having a value of 1, 2, 3 or 4;
R$_1$ is hydrogen, halogen, halosubstituted C$_{1-8}$ alkyl, C$_{1-8}$ alkyl, hydroxy, C$_{1-8}$alkoxy, halosubstitutedC$_{1-8}$ alkoxy, —(CH$_2$)$_t$aryl, O—(CH$_2$)$_t$ aryl, O—CH$_2$—O-C$_{1-8}$alkyl, O—(CH$_2$)$_v$C(O)OC$_{1-4}$alkyl, NO$_2$, S(O)$_m$R$_2$, N(R$_3$)$_2$, NHC(O)R$_4$, —C(O)R$_5$; or together two R$_1$ moieties may form a methylene dioxy ring system or together two R$_1$ moieties may form a 6 membered saturated or unsaturated ring system which may be optionally substituted;

s is an integer having a value of 1, 2, or 3;

v is an integer having a value of 1, 2, 3, or 4;

m is 0 or an integer having a value of 1 or 2;

t is 0 or an integer having a value of 1, 2, 3 or 4;

R$_2$ is an optionally substituted C$_{1-8}$ alkyl;

R$_3$ is independently hydrogen, or C$_{1-4}$ alkyl, or together with the nitrogen to which they are attached form a 5 to 7 membered saturated or unsaturated ring;

R$_4$ is independently hydrogen, or C$_{1-4}$ alkyl;

R$_5$ is hydrogen, optionally substituted C$_{1-8}$ alkyl, or C$_{1-8}$ alkoxy; provided that when R$_1$ is hydrogen, s is 1, X is O, n=1 than R$_6$ is other than an unsubstituted phenyl;

when s=3, R$_1$ is a 4-5 methylene dioxy ring, 2- chloro, n=1, X=O, then R$_6$ is other than a 2,6-difluoro substituted phenyl;

when s=3, R$_1$ is a 4-5 methylene dioxy ring, 2- chloro, n=1, X=O , then R$_6$ is other than a 2,- or 4- C(O)$_2$H substituted phenyl;

when s=3, R$_1$ is a 4-5 methylene dioxy ring, 2- chloro, n=1, X=O, then R$_6$ is other than a 3-phenyloxy substituted phenyl;

or pharmaceutically acceptable salts thereof.

DETAILED DESCRIPTION OF THE INVENTION

The novel compounds of Formula (I) may also be used in association with the veterinary treatment of mammals, other than humans, in need of inhibition of IL-8 or other chemokines which bind to the IL-8 a and b receptors. Chemokine mediated diseases for treatment, therapeutically or prophylactically, in animals include disease states such as those noted herein in the Methods of Treatment section.

Suitably R$_6$ is an optionally substituted C$_{3-7}$ cycloalkyl, optionally substituted C$_{3-7}$ cycloalkenyl, or optionally substituted aryl; wherein n is 0 or an integer having a value of 1, 2, 3 or 4. Preferably, R$_6$ is an optionally substituted O—(CR$_8$R$_9$)$_n$-aryl, wherein the aryl is phenyl, and n is preferably 1, such as in a benzyloxy group.

The R$_6$ cycloalkyl, cycloalkenyl and aryl rings may be optionally substituted one or more times independently by halogen; hydroxy; hydroxy substituted C$_{1-10}$alkyl; C$_{1-10}$ alkyl, such as methyl, ethyl, propyl, isopropyl, or t-butyl; halosubstituted C$_{1-10}$ alkyl, such CF$_3$; C$_{1-10}$ alkoxy, such as methoxy, ethoxy, isopropyloxy, or propyloxy; optionally substituted C$_{1-10}$ alkoxy, such as methoxymethoxy or trifluoromethoxy; S-C$_{1-10}$ alkyl, such as methyl thio; C(O)C$_{1-10}$alkyl such as 2,2-dimethylpropanoyl; C(O)$_2$H; cyano, nitro; aryloxy, such as phenoxy (wherein the aryl ring may be optionally substituted as defined herein); an optionally substituted aryl, such as phenyl, an optionally substituted arylalkyl, such as benzyl or phenethyl, an optionally substituted heteroaryl, such as tetrazole, or an optionally substituted heteroarylalkyl, wherein these aryl and heteroaryl moieties may be substituted one to two times by halogen; hydroxy; bydroxy substituted alkyl; C$_{1-10}$ alkoxy; S(O)$_m$ C$_{1-10}$ alkyl, wherein m is 0, 1 or 2; amino, mono & di-substituted amino, such as in the N(R$_3$)$_2$ group; C$_{1-10}$ alkyl, or halosubstituted C$_{1-10}$ alkyl, such as CF$_3$.

Suitably when R$_6$ is a C$_{3-7}$ cycloalkyl moiety it is preferably a cyclohexyl ring, such as in cyclohexylmethoxy.

Suitably X is oxygen or C(O)NH—, preferably oxygen. When X is C(O)NH, R$_6$ is preferably aryl and n is 0.

Suitably R$_1$ is hydrogen, halogen, halosubstituted C$_{1-8}$ alkyl, C$_{1-8}$ alkyl, hydroxy, C$_{1-8}$alkoxy, halosubstitutedC$_{1-8}$ alkoxy, O—CH$_2$—O-C$_{1-8}$alkyl, —(CH$_2$)$_t$aryl, O—(CH$_2$)$_t$ aryl, —O—(CH$_2$)$_v$C(O)OC$_{1-4}$alkyl, NO$_2$, S(O)$_m$R$_2$, N(R$_3$)$_2$, NHC(O)R$_4$, —C(O)R$_5$, or together two R$_1$ moieties may form a methylene dioxy ring system, or together two R$_1$ moieties may form a 6 membered saturated or unsaturated ring system which may be optionally substituted; wherein s is an integer having a value of 1, 2, 3, or 4; t is 0 or an integer having a value of 1, 2, 3, or 4; v is an integer having a value of 1, 2, 3, or 4; and m is 0 or an integer having a value of 1 or 2.

Preferably when the phenyl ring is monosubstituted, the R$_1$ group is in the 4-position. When the phenyl ring is substituted by a methylenedioxy group it is preferably in the 3,4-position; and more preferably the phenyl ring may also be additionally substituted by another R$_1$, such as halogen, preferably fluorine or chlorine. When the two R$_1$ moieties form a 6 membered saturated or unsaturated ring system, which may contain 0 to 2 double bonds, and is preferably an aromatic ring forming a naphthyl ring system, which ring may be optionally substituted as defined herein. Preferred substituents for R$_1$ are NO$_2$, OCF$_3$, OCH$_3$, CH$_3$, benzyloxy, phenoxy, hydrogen or halogen, preferably fluorine or chlorine, more preferably chlorine.

Suitably, R$_2$ is an optionally substituted C$_{1-8}$ alkyl.

Suitably, R$_3$ is independently hydrogen, or C$_{1-4}$ alkyl, or together with the nitrogen to which they are attached form a 5 to 7 membered saturated or unsaturated ring; such as such as pyrrole, piperidine, or pyridine.

Suitably, R$_4$ is independently hydrogen, or C$_{1-4}$ alkyl.

Suitably, R$_5$ is hydrogen, optionally substituted C$_{1-8}$ alkyl, or C$_{1-8}$ alkoxy.

Suitably, R$_8$ and R$_9$ are independently hydrogen or C$_{1-4}$ alkyl.

Exemplified compounds of Formula (I) include:

1-(2-chloro-4,5-methylenedioxybenzyl)-5-(4-methoxybenzyloxy)indole-2-carboxylic acid;

1-(2-chloro-4,5-methylenedioxybenzyl)-5-(4-trifluoromethylbenzyloxy)indole-2-carboxylic acid;

5-benzyloxy-1-(2-chloro-4,5-methylenedioxybenzyl) indole-2-carboxylic acid;

1-(2-chloro-4,5-methylenedioxybenzyl)-5-(3-trifluoromethylbenzyloxy)indole-2-carboxylic acid;

1-(2-chloro-4,5-methylenedioxybenzyl)-5-[(R)-1-phenylethoxy]indole-2-carboxylic acid;

1-(2-chloro-4,5-methylenedioxybenzyl)-5-(2-trifluoromethylbenzyloxy)indole-2-carboxylic acid;

1-(2-chloro-4,5-methylenedioxybenzyl)-5-(2-methoxybenzyloxy)indole-2-carboxylic acid;

1-(2-chloro-4,5-methylenedioxybenzyl)-5-(2,6-dichlorobenzyloxy)indole-2-carboxylic acid;

1-(2-chloro-4,5-methylenedioxybenzyl)-5-[(S)-1-phenylethoxy]indole-2-carboxylic acid;

1-(2-chloro-4,5-methylenedioxybenzyl)-5-(4-carboxybenzyloxy)indole-2-carboxylic acid; 1-(2-chloro-4,5-methylenedioxybenzyl)-5-(3-methoxybenzyloxy)indole-2-carboxylic acid;

1-(2-chloro-4,5-methylenedioxybenzyl)-5-cyclohexylmethoxyindole-2-carboxylic acid;

1-(2-chloro-4,5-methylenedioxybenzyl)-5-(3-carboxybenzyloxy)indole-2-carboxylic acid;

1-(2-chloro-4,5-methylenedioxybenzyl)-5-[4-(1H)-tetrazolylbenzyloxy]indole-2-carboxylic acid;

1-(2-chloro-4,5-methylenedioxybenzyl)-5-(N-phenylcarboxamido)indole-2-carboxylic acid;

1-(2-chloro-4,5-methylenedioxybenzyl)-5-(2-phenoxybenzyloxy)indole-2-carboxylic acid.

As used herein, "optionally substituted" unless specifically defined shall mean such groups as halogen, such as fluorine, chlorine, bromine or iodine; hydroxy; hydroxy substituted $C_{1-10}$alkyl; $C_{1-10}$ alkoxy, such as methoxy or ethoxy; S(O)m $C_{1-10}$ alkyl, wherein m is 0, 1 or 2, such as methyl thio, methylsulfinyl or methyl sulfonyl; amino, mono & di-substituted amino, such as in the $N(R_3)_2$ group; $C_{1-10}$ alkyl, such as methyl, ethyl, propyl, isopropyl, or t-butyl; halosubstituted $C_{1-10}$ alkyl, such $CF_3$; an optionally substituted aryl, such as phenyl, or an optionally substituted arylalkyl, such as benzyl or phenethyl, wherein these aryl moieties may be substituted one to two times by halogen; hydroxy; hydroxy substituted alkyl; $C_{1-10}$ alkoxy; $S(O)_m$ $C_{1-10}$ alkyl; amino, mono & di-substituted amino, such as in the $N(R_3)_2$ group; $C_{1-10}$ alkyl, or halosubstituted $C_{1-10}$ alkyl, such as $CF_3$.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of Formula (I) may also be formed with a pharmaceutically acceptable cation, for instance, if a substituent group comprises a carboxy moiety. Suitable pharmaceutically acceptable cations are well known to those skilled in the art and include alkaline, alkaline earth, ammonium and quaternary ammonium cations.

A preferred salt form of the compounds of Formula (I) is the sodium salt.

The following terms, as used herein, refer to:

"halo"—all halogens, that is chloro, fluoro, bromo and iodo.

"$C_{1-10}$alkyl" or "alkyl"—both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

"cycloalkyl" is used herein to mean cyclic radicals, preferably of 3 to 8 carbons, including but not limited to cyclopropyl, cyclopentyl, cyclohexyl, and the like.

"cycloalkenyl" is used herein to mean cyclic radicals, preferably of 3 to 8 carbons, having one or more bonds which are unsaturated, including but not limited to cyclopentenyl, or cyclohexenyl.

"alkenyl" is used herein at all occurrences to mean straight or branched chain radical of 2–10 carbon atoms, unless the chain length is limited thereto, including, but not limited to ethenyl, 1-propenyl, 2-propenyl, 2-methyl-1-propenyl, 1-butenyl, 2-butenyl and the like.

"aryl"—phenyl and naphthyl ring.

"heteroaryl" (on its own or in any combination, such as "heteroaryloxy", or "heteroaryl alkyl")—a 5–10 membered aromatic ring system in which one or more rings contain one or more heteroatoms selected from the group consisting of N, O or S, such as, but not limited, to pyrrole, pyrazole, furan, thiophene, quinoline, isoquinoline, quinazolinyl, pyridine, pyrimidine, oxazole, thiazole, thiadiazole, triazole, imidazole, or benzimidazole.

"heterocyclic" (on its own or in any combination, such as "heterocyclylalkyl")—a saturated or partially unsaturated 4–10 membered ring system in which one or more rings contain one or more heteroatoms selected from the group consisting of N, O, or S; such as, but not limited to, pyrrolidine, piperidine, piperazine, morpholine, tetrahydropyran, or imidazolidine.

The term "aralkyl" or "heteroarylalkyl" or "heterocyclicalkyl" is used herein to mean $C_{1-8}$ alkyl as defined above attached to an aryl, heteroaryl or heterocyclic moiety, as also defined herein, unless otherwise indicated.

"sulfinyl"—the oxide S (O) of the corresponding sulfide, the term "thio" refers to the sulfide, and the term "sulfonyl" refers to the fully oxidized $S(O)_2$ moiety.

The compounds of Formula (I) may be obtained by applying synthetic procedures, some of which are illustrated in the Schemes below. The synthesis provided for in these Schemes is applicable for the producing compounds of Formula (I) having a variety of different R, and $R_1$ groups which are reacted, employing optional substituents which are suitably protected, to achieve compatibility with the reactions outlined herein. Subsequent deprotection, in those cases, then affords compounds of the nature generally disclosed. Once the indole nucleus has been established, further compounds of Formula (I) may be prepared by applying standard techniques for functional group interconversion, well known in the art.

Compounds of the formula I wherein $R^1$=alkyl or aralkyl are prepared by methods analogous to those described in Scheme 1.

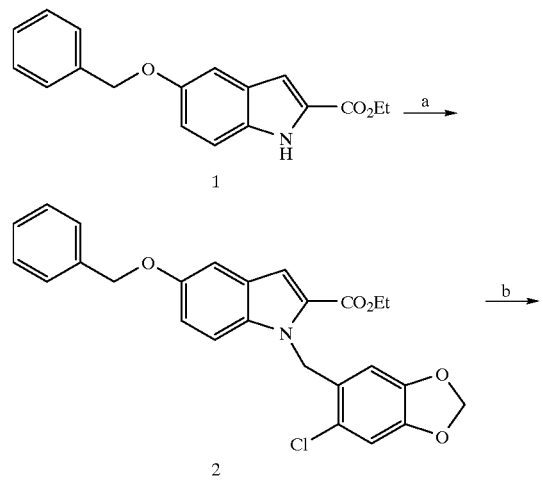

Scheme 1

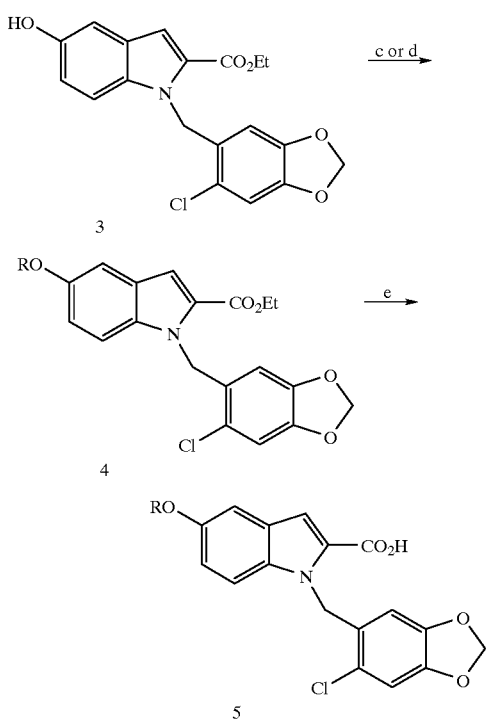

a) NaH, DMF, 6-chloropiperonyl chloride; b) H₂, Pd—C, EtOAc; c) NaH, DMF, R—Cl or R—Br; d) ROH, PPh₃, DEAD, THF e) KOH, THF, EtOH, H₂O 1-Scheme 1 is alkylated by treatment with a strong base (such as sodium hydride or potassium hydride) in an aprotic solvent (such as DMF or THF) and 6-chloropiperonyl chloride to provide 2-Scheme 1. Treatment of 2-Scheme 1 with a suitable hydrogenation catalyst (such as palladium on carbon) under a hydrogen atmosphere in a polar solvent (such as ethyl acetate or ethanol) should provide 3-Scheme 1. This material may be alkylated by treatment with a strong base (such as sodium hydride or potassium hydride) in an aprotic solvent (such as DMF or THF) and an alkyl halide. Alternatively, 4-Scheme 1 may be prepared by treatment with a primary or secondary alcohol (such as benzyl or heterocycle-substituted benzyl), triphenylphosphine and an azodicarboxylic ester (such as diethyl azodicarboxylate or diisopropylazodicarboxylate) in an aprotic solvent (such as THF or N-methylmorpholine). 4-Scheme 1 may be saponified by treatment with a hydroxide base (such as potassium hydroxide, sodium hydroxide or lithium hydroxide) to yield carboxylic acid 5-Scheme 1.

Scheme 2

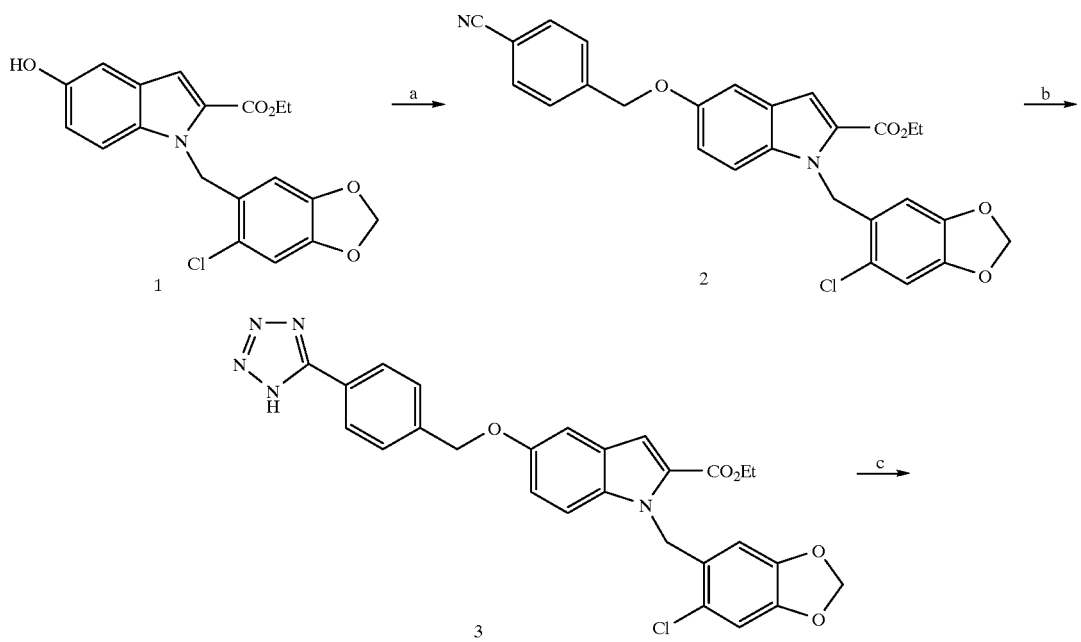

-continued

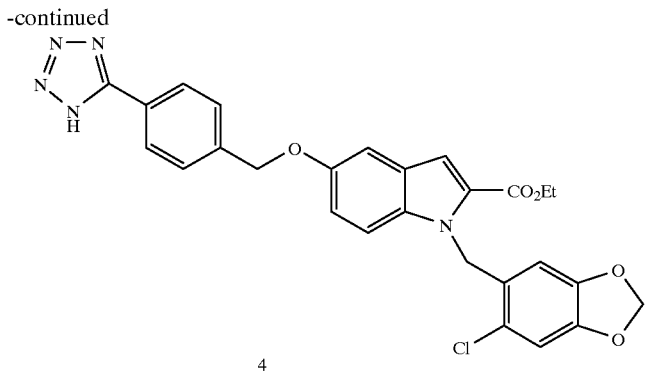

4 a) NaH, DMF, 4-cyanobenzyl bromide; b) NaN₃, Me₃SnCl, PhMe; c) KOH, THF, EtOH, H₂O Compounds of the formula I wherein $R^1$ is 4-(2-tetrazolyl)benzyl are prepared by methods analogous to those described in Scheme 2. Treatment of 1-Scheme 2 with a strong base (such as sodium hydride or potassium hydride) in an aprotic solvent (such as DMF or THF) and 4-cyanobenzyl bromide provides 2-Scheme 2. This material is converted to the tetrazole 3-Scheme 2 by treatment with sodium azide and trimethyltin chloride in toluene. 3-Scheme 2 may be saponified by treatment with a hydroxide base (such as potassium hydroxide, sodium hydroxide or lithium hydroxide) to yield carboxylic acid 4-Scheme 2.

Pharmaceutically acid addition salts of compounds of Formula (I) may be obtained in known manner, for example by treatment thereof with an appropriate amount of acid in the presence of a suitable solvent.

In the Examples, all temperatures are in degrees Centigrade (° C.). Mass spectra were performed upon a VG Zab mass spectrometer using fast atom bombardment, unless otherwise indicated. ¹H-NMR (hereinafter "NMR") spectra were recorded at 250 MHz or 400 MHz using a Bruker AM 250 or Am 400 spectrometer, respectively. Multiplicities indicated are: s=singlet, d=doublet, t=triplet, q=quartet, m=multiplet and br indicates a broad signal. Sat. indicates a saturated solution, eq indicates the proportion of a molar equivalent of reagent relative to the principal reactant.

Flash chromatography is run over Merck Silica gel 60 (230–400 mesh).

SYNTHETIC EXAMPLES

The invention will now be described by reference to the following examples which are merely illustrative and are not to be construed as a limitation of the scope of the present invention. All temperatures are given in degrees centigrade, all solvents are highest available purity and all reactions run under anydrous conditions in an argon atmosphere unless otherwise indicated.

Example 1

Preparation of 1-(2-chloro-4,5-methylenedioxybenzyl)-5-(4-methoxybenzyloxy)indole-2-carboxylic acid a) ethyl 5-benzyloxy-1-(2-chloro-4,5-methylenedioxybenzyl)indole-2-carboxylate To a stirring suspension of sodium hydride (2.03grams (hereinafter "g"), (60% in mineral oil), 50.8 millimoles (hereinafter "mmol")) in DMF (100 milliliters (hereinafter "mL")) was added ethyl 5-benzyloxyindole-2-carboxylate (10.0 g, 33.9 mmol). After 10 minutes (hereinafter "min"), 6-chloropiperonyl chloride (10.4 g, 50.8 mmol) was added. After 1 hour, the mixture was partitioned between water and ethyl acetate. The organic layer was washed with water and saturated brine, dried (MgSO₄), filtered and concentrated to leave an oily pale yellow solid. The solid was recrystallized from ethanol to provide the title compound as a white solid (7.8 g, 50%). ¹HNMR (400 MHz, CDCl₃) d 7.49–7.33 (m, 6H), 7.19–7.08 (m, 3H), 6.87 (s, 1H), 5.86 (s, 2H), 5.78 (s, 1H), 5.77 (s, 2H), 5.11 (s, 2H), 4.33 (q, 2H), 1.36 (t, 3H).

b) ethyl 1-(2-chloro-4,5-methylenedioxybenzyl)-5-hydroxyindole-2-carboxylate

The compound of Example 1(a) (7.8 g, 16.8 mmol) was dissolved in ethyl acetate (250 mL) and to the solution was added 10% palladium on carbon (3.9 g, 50% w/w). The mixture was placed on a Parr shaker at 60 p.s.i. for 16 hours, then filtered through Celite. The solution was concentrated to give a residue that was purified by column chromatography (silica gel, ethyl acetate/hexane) to give the title compound as a white solid (4.71 g, 75%). ¹HNMR (400 MHz, CDCl₃) d 7.31 (m, 1H), 7.11 (m, 2H), 6.91 (m, 1H), 6.89 (s, 1H), 5.86 (s, 2H), 5.79 (s, 1H), 5.75 (s, 2H), 4.62 (s, 1H), 4.32 (q, 2H), 1.33 (t, 3H).

c) ethyl 1-(2-chloro-4,5-methylenedioxybenzyl)-5-(4-methoxybenzyloxy)indole-2-carboxylate The compound of Example 1(b) (0.110 g, 0.294 mmol), 4-methoxybenzyl alcohol (0.061 g, 0.441 mmol), and triphenylphosphine (0.116 g, 0.441 mmol) were dissolved in N-methylmorphiline (2 mL) and taken to 0_C when diisopropylazodicarboxylate (0.089 g, 0.441 mmol) was added dropwise. The solution was allowed to warm to room temperature and stir for 16 hours when concentrated. The resulting residue was chromatographed (silica gel, ethyl acetate/hexane) to provide the title compound as a white solid (0.060 g, 41%). ¹ HNMR (400 MHz, CDCl₃) d 7.42 (m, 2H), 7.20–7.04 (m, 4H), 6.92 (m, 3H), 5.88 (s, 2H), 5.80 (s, 1H), 5.77 (s, 2H), 5.03 (s, 2H), 4.34 (q, 2H), 3.83 (s, 3H), 1.37 (t, 3H).

d) 1-(2-chloro-4,5-methylenedioxybenzyl)-5-(4-methoxybenzyloxy)indole-2-carboxylic acid The compound of Example 1(c) (0.060 g, 0.121 mmol) was dissolved in 1.5 mL of 1:1 THF/ethanol and 3N potassium hydroxide (1.2 mL) was added. The mixture was heated at reflux for 1.5 hours then diluted with ethyl acetate and acidified with 3N HCl. The organic layer was washed with saturated brine, dried (MgSO₄), filtered and concentrated to provide the title compound (0.056 g, 100%) The title compound was converted to the sodium salt using 1.0 equivalents of 0.1N sodium hydroxide in ethanol. MS (MH⁺): 466.0.

Example 2

Preparation of 1-(2-chloro-4,5-methylenedioxybenzyl)-5-(4-trifluoromethylbenzyloxy)-indole-2-carboxylic acid a) ethyl 1-(2-chloro-4,5-methylenedioxybenzyl)-5-(4-trifluoromethylbenzyloxy)indole-2-carboxylate To a stirring suspension of sodium hydride (0.016 g, (60% in mineral oil), 0.402 mmol) in DMF (2 mL) was added ethyl 1-(2-chloro-4,5-methylenedioxybenzyl)-5-hydroxyindole-2-carboxylate (0.100 g, 0.268 mmol). After 15 minutes, 4-trifluoromethylbenzyl bromide (0.096 g, 0.402 mmol) was added. After 1.5 hours, the mixture was partitioned between water and ethyl acetate. The organic layer was washed with water and saturated brine, dried ($MgSO_4$), filtered and concentrated to a residue that was purified by column chromatography (ethyl acetate/hexane) to give the title compound as a white solid (0.124 g, 87%).
$^1$HNMR (400 MHz, $CDCl_3$) d 7.66 (d, 2H), 7.59 (d, 2H), 7.32 (s, 1H), 7.16 (m, 2H), 7.08 (m, 1H), 6.88 (s, 1H), 5.86 (s, 2H), 5.79 (s, 1H), 5.78 (s, 2H), 5.17 (s, 2H), 4.33 (q, 2H), 1.37 (t, 3H).

b) 1-(2-chloro-4,5-methylenedioxybenzyl)-5-(4-trifluoromethylbenzyloxy)indole-2-carboxylic acid Following the procedure of Example 1(d), except substituting ethyl 1-(2-chloro-4,5-methylenedioxybenzyl)-5-(4-trifluoromethylbenzyloxy)indole-2-carboxylate for ethyl 1-(2-chloro-4,5-methylenedioxybenzyl)-5-(4-methoxybenzyloxy)indole-2-carboxylate, the title compound was prepared as a white solid (0.115 g, 100%).
$^1$HNMR (400 MHz, $CD_3OD$) d 7.58 (m, 4H), 7.13 (m, 1H), 7.05 (m, 2H), 6.89 (m, 1H), 6.78 (s, 1H), 5.89 (s, 2H), 5.80 (s, 1H), 5.78 (s, 2H), 5.13 (s, 2H).

Example 3

Preparation of 5-benzyloxy-1-(2-chloro-4,5-methylenedioxybenzyl)indole-2-carboxylic acid Following the procedure of Example 2(a)–2(b), except substituting benzyl bromide for 4-trifluoromethylbenzyl bromide in step (a), the title compound was prepared as a white solid (82% overall). $^1$HNMR (400 MHz, $CDCl_3$) d 7.42–7.35 (m, 6H), 7.15–7.08 (m, 2H), 7.00 (m, 1H), 6.81 (s, 1H), 5.81 (s, 2H), 5.72 (s, 1H), 5.70 (s, 2H), 5.06 (s, 2H).

Example 4

Preparation of 1-(2-chloro-4,5-methylenedioxybenzyl)-5-(3-trifluoromethylbenzyloxy)indole-2-carboxylic acid Following the procedure of Example 2(a)–2(b) except substituting 3-trifluoromethylbenzyl bromide for 4-trifluoromethylbenzyl bromide in step (a), the title compound was prepared as a white solid (0.103 g, 76% overall). MS ($MH^+$): 502.0.

Example 5

Preparation of 1-(2-chloro-4,5-methylenedioxybenzyl)-5-[(R)-1-phenylethoxy]indole-2-carboxylic acid Following the procedure of Example 1(a)–1(d) except substituting (R)-(+)-sec-phenethyl alcohol for 4-methoxybenzyl alcohol in step (c), the title compound was prepared as a yellow solid (0.055 g, 38% overall). MS ($MH^+$): 450.0.

Example 6

Preparation of 1-(2-chloro-4,5-methylenedioxybenzyl)-5-(2-trifluoromethylbenzyloxy)indole-2-carboxylic acid Following the procedure of Example 1(a)–1(d) except substituting 2-trifluoromethylbenzyl alcohol for 4-methoxybenzyl alcohol in step (c), the title compound was prepared as a white solid (0.1 14 g, 68% overall). MS ($MH^-$): 502.0.

Example 7

Preparation of 1-(2-chloro-4,5-methylenedioxybenzyl)-5-(2-methyloxybenzyloxy)indole-2-carboxylic acid Following the procedure of Example 1(a)-i(d) except substituting b 2-methoxybenzyl alcohol for 4-methoxybenzyl alcohol in step (c), the title compound was prepared as a white solid (0.083 g, 50% overall). MS ($MH^-$): 464.0.

Example 8

Preparation of 1-(2-chloro-4,5-methylenedioxybenzyl)-5-(2,6-dichlorobenzyloxy)indole-2-carboxylic acid Following the procedure of Example 2(a)–2(b) except substituting 2,6-dichlorobenzyl bromide for 4-trifluoromethylbenzyl bromide in step (a), the title compound was prepared as a white solid (0.096 g, 71% overall). MS ($MH^+$): 504.0.

Example 9

Preparation of 1-(2-chloro-4,5-methylenedioxybenzyl)-5-[(S)-1-phenylethoxy]indole-2-carboxylic acid Following the procedure of Example 1(a)–1(d) except substituting (S)-(–)-sec-phenethyl alcohol for 4-methoxybenzyl alcohol in step (c), the title compound was prepared as a yellow solid (0.068 g, 45% overall). MS ($MH^-$): 448.2.

Example 10

Preparation of 1-(2-chloro-4,5-methylenedioxybenzyl)-5-(4-carboxybenzyloxy)indole-2-carboxylic acid Following the procedure of Example 2(a)–2(b) except substituting methyl 4-(bromomethyl)benzoate for 4-trifluoromethylbenzyl bromide in step (a), the title compound was prepared as a white solid (30% overall). MS ($MH^-$): 478.0.

Example 11

Preparation of 1-(2-chloro-4,5-methylenedioxybenzyl)-5-(3-methyloxybenzyloxy)indole-2-carboxylic acid Following the procedure of Example 2(a)–2(b) except substituting 3-methoxybenzyl chloride for 4-trifluoromethylbenzyl bromide in step (a), the title compound was prepared as a white solid (0.082 g, 66% overall). MS ($MH^+$): 466.0.

Example 12

Preparation of 1-(2-chloro-4,5-methylenedioxybenzyl)-5-cyclohexylmethoxyindole-2-carboxylic acid Following the procedure of Example 2(a)–2(b) except substituting cyclohexylmethylbromide for 4-trifluoromethylbenzyl bromide in step (a), the title compound was prepared as a white solid (0.083 g, 70% overall). MS (MH$^+$): 442.0.

Example 13

Preparation of 5-(3-carboxybenzyloxy)-1-(2-chloro-4,5-methylenedioxybenzyl)indole-2-carboxylic acid Following the procedure of Example 2(a)–2(b) except substituting methyl 3-(bromomethyl)benzoate for 4-trifluoromethylbenzyl bromide in step (a), the title compound was prepared as a white solid (0.090 g, 70% overall). MS (MH$^-$): 478.0.

Example 14

Preparation of 1-(2-chloro-4,5-methylenedioxybenzyl)-5-[4-(1H)-tetrazolylbenzyloxy]indole-2-carboxylic acid a) ethyl 1-(2-chloro-4,5-methylenedioxybenzyl)-5-(4-cyanobenzyloxy)indole-2-carboxylate Following the procedure of Example 2(a) except substituting a-bromo-p-tolunitrile for 4-trifluoromethylbenzyl bromide, the title compound was prepared as a white solid (0.260 g, 0.532 mmol). $^1$HNMR (400 MHz, CDCl$_3$) d 7.72 (d, 2H), 7.59 (d, 2H), 7.35 (s, 1H), 7.17 (m, 2H), 7.06 (m, 1H), 6.89 (s, 1H), 5.89 (s, 2H), 5.77 (s, 3H), 5.14 (s, 2H), 4.33 (q, 2H), 1.35 (t, 3H).

b) ethyl 1-(2-chloro-4,5-methylenedioxybenzyl)-5-[4-(1H)-tetrazolylbenzyloxy)indole-2-carboxylate A mixture of trimethyltin chloride (0.489 g, 2.46 mmol) and sodium azide (0.200 g, 3.07mmol) were stirred in toluene (10 mL) for 10 minutes, when the compound of Example 14 (a) (0.150 g, 0.307 mmol) was added. The mixture was then stirred at reflux temperature for 48 hours when a 1:1 mixture of methanol/1N hydrochloric acid (10 mL) was added and stirred at room temperature for 2 hours. The mixture was then diluted with ethyl acetate and washed successively with water and saturated brine. The organic layer was collected, dried over MgSO$_4$, filtered and concentrated to a residue that was purified by column chromatography (silica gel, methanol/methylene chloride) to yield the title compound as a white solid (0.121 g, 0.227 mmol). $^1$HNMR (400 MHz, CD$_3$OD) d 8.01 (d, 2H), 7.58 (d, 2H), 7.32 (s, 1H), 7.12 (m, 3H), 6.83 (s, 1H), 5.81 (s, 2H), 5.71 (s, 1H), 5.69 (s, 2H), 5.14 (s, 2H), 4.26 (q, 2H), 1.29 (t, 3H).

c) 1-(2-chloro-4,5-methylenedioxybenzyl)-5-[4-(1H)-tetrazolylbenzyloxy]indole-2-carboxylic acid Following the procedure of Example 1(d), except substituting ethyl 1-(2-chloro-4,5-methylenedioxybenzyl)-5-[4-(1H)-tetrazolylbenzyloxy)indole-2-carboxylate for ethyl 1-(2-chloro-4,5-methylenedioxybenzyl)-5-(4-methoxybenzyloxy)indole-2-carboxylate, the title compound was prepared as an off-white solid (0.096 g, 63% overall). MS (MH$^-$): 502.3.

Example 15

Preparation of 1-(2-chloro-4,5-methylenedioxybenzyl)-5-(N-phenylcarboxamido)indole-2-carboxylic acid a) ethyl 1-(2-chloro-4,5-methylenedioxybenzyl)-5-trifluoromethanesulfonyloxyindole-2-carboxylate A solution of the compound of Example 1(b) (832 mg, 2.2 mmol) and N-phenyltrifluoromethanesulfonimide (816.9 mg, 2.27 mmol) in 6 mL of dry methylene chloride was cooled in an ice bath, and triethylamine (240.8 mg, 2.38 mmol, 0.33 mL) was added over 30 minutes. The resulting mixture was held at 0° C. for 1 hour and allowed to warm to room temperature. The reaction mixture was stirred at room temperature for 16 hours. Then the reaction mixture was diluted with ether and washed with water, 1N NaOH (2×), water and brine. The organic layer was dried over MgSO$_4$, filtered and concentrated under reduced pressure to give the title compound (1.05 g, 93%). MS (M+H$^+$): 490.0.

b) ethyl 1-(2-chloro-4,5-methylenedioxybenzyl)-5-(N-phenylcarboxamido)indole-2-carboxylate A mixture of the compound of Example 15(a) (355 mg, 0.7 mmol), triethylamine (141.7 mg, 1.4 mmol, 0.2 mL), triphenylphosphine (12 mg, 0.042 mmol), palladium acetate (5 mg, 0.021 mmol) and aniline (1.30 g, 14 mmol, 1.27 mL) in DMF (4 mL) was purged with carbon monoxide for 5 minutes and stirred under a CO ballon at 60° C. for 16 h, then cooled to room temperature. The reaction mixture was diluted with brine, extracted with ether, washed with 1N HCl and then brine until neutral. The organic layer was dried over MgSO$_4$, filtered and concentrated under reduced pressure and chromatography of the resulting liquid on silica gel (hexane: ethyl acetate; 1:1) the title compound (270 mg, 78%). MS (M+H$^+$): 477.1.

c) 1-(2-chloro-4,5-methylenedioxybenzyl)-5-(N-phenylcarboxamido)indole-2-carboxylic acid Following the procedure of Example 1(d), except substituting ethyl 1-(2-chloro-4,5-methylenedioxybenzyl)-5-(N-phenylcarboxamido)indole-2-carboxylate ethyl 1-(2-chloro-4,5-methylenedioxybenzyl)-5-(4-methoxybenzyloxy)indole- 2-carboxylate, the title compound was prepared as a white solid (122 mg, 93%). MS (M+H$^+$): 448.0.

Example 16

Preparation of 1-(2-Chloro-4,5-methlenedioxybenzyl)-5-(2-phenoxybenzyloxy)indole-2-carboxylic acid a) 2-phenoxybenzyl alcohol 2-Phenoxybenzoic acid (2.5 g, 11.7 mmol) was dissolved in THF and added dropwise over 15 min to a solution of lithium aluminum hydride (443 mg, 11.7 mmol) in THF. After 5 min, water (0.44 mL) was added slowly, followed by 15% aqueous NaOH (0.44 mL) and water (1.33 mL). The solid was removed by vacuum filtration and the filtrate was concentrated to give the title compound (2.1 g, 90%).

$^1$H NMR (400 MHz, d$^6$-DMSO) d 7.59 (dd, 1H), 7.39 (m, 2H), 7.3 (m, 1H), 7.2 (t, 1H), 7.1 (t, 1H), 6.92(d, 2H), 6.89 (d, 1H).

b) ethyl 1-(2-Chloro-4,5-methlenedioxybenzyl)-5-(2-phenoxybenzyloxy)indole-2-carboxylate Following the procedure of Example 1(c)–1(d) except substituting 2-phenoxybenzyl alcohol for 4-methoxybenzyl alcohol in step (c), the title compound was prepared as a white solid (243 mg, 95%). MS (M–H$^-$): 526.0.

METHODS OF TREATMENT

The compounds of Formula (I) or a pharmaceutically acceptable salt thereof can be used in the manufacture of a medicament for the prophylactic or therapeutic treatment of any disease state in a human, or other mammal, which is exacerbated or caused by excessive or unregulated IL-8 cytokine production by such mammal's cell, such as but not limited to monocytes and/or macrophages, or other chemokines which bind to the IL-8 a or b receptor, also referred to as the type I or type II receptor.

Accordingly, the present invention provides a method of treating a chemokine mediated disease, wherein the chemokine is one which binds to an IL-8 a or b receptor and which method comprises administering an effective amount of a compound of Formula (I) or a pharmaceutically acceptable salt thereof. In particular, the chemokines are IL-8, GROα, GROβ, GROγ, NAP-2 or ENA-78.

The compounds of Formula (I) are administered in an amount sufficient to inhibit cytokine function, in particular IL-8, GROα, GROβ, GROγ, NAP-2 or ENA-78, such that they are biologically regulated down to normal levels of physiological function, or in some case to subnormal levels, so as to ameliorate the disease state. Abnormal levels of IL-8, GROα, GROβ, GROγ, NAP-2 or ENA-78 for instance in the context of the present invention, constitute: (i) levels of free IL-8 greater than or equal to 1 picogram per mL; (ii) any cell associated IL-8, GROα, GROβ, GROγ, NAP-2 or ENA-78 above normal physiological levels; or (iii)the presence IL-8, GROα, GROβ, GROγ, NAP-2 or ENA-78 above basal levels in cells or tissues in IL-8, GROα, GROβ, GROγ, NAP-2 or ENA-78 respectively, is produced.

There are many disease states in which excessive or unregulated IL-8 production is implicated in exacerbating and/or causing the disease. Chemokine mediated diseases include psoriasis, atopic dermatitis, arthritis, asthma, chronic obstructive pulmonary disease, adult respiratory distress syndrome, inflammatory bowel disease, Crohn's disease, ulcerative colitis, stroke, septic shock, endotoxic shock, gram negative sepsis, toxic shock syndrome, cardiac and renal reperfusion injury, glomerulonephritis, thrombosis, graft vs. host reaction, alzheimers disease, allograft rejections, malaria, restinosis, angiogenesis or undesired hematopoietic stem cells release.

These diseases are primarily characterized by massive neutrophil infiltration, T-cell infiltration, or neovascular growth, and are associated with IL-8, GROα, GROβ, GROγ, or NAP-2 production which is responsible for the chemotaxis of neutrophils into the inflammatory site or the directional growth of endothelial cells. In contrast to other inflammatory cytokines (IL-1, TNF, and IL-6), with IL-8, GROα, GROβ, GROγ, or NAP-2 has the unique property of promoting neutrophil chemotaxis, enzyme release including but not limited to elastase release as well as superoxide production and activation. The a-chemokines but particularly, with IL-8, GROα, GROβ, GROγ, or NAP-2, working through the IL-8 type I or II receptor can promote the neovascularization of tumors by promoting the directional growth of endothelial cells. Therefore, the inhibition of IL-8 induced chemotaxis or activation would lead to a direct reduction in the neutrophil infiltration.

The compounds of Formula (I) are administered in an amount sufficient to inhibit IL-8, binding to the IL-8 alpha or beta receptors, from binding to these receptors, such as evidenced by a reduction in neutrophil chemotaxis and activation. The discovery that the compounds of Formula (I) are inhibitors of IL-8 binding is based upon the effects of the compounds of Formulas (I) in the in vitro receptor binding assays which are described herein. The compounds of Formula (I) have been shown to be dual inhibitors of both recombinant type I and type II IL-8 receptors. Preferably the compounds are inhibitors of only one receptor, preferably Type II.

As used herein, the term "IL-8 mediated disease or disease state" refers to any and all disease states in which with IL-8, GROα, GROβ, GROγ, or NAP-2 plays a role, either by production of with IL-8, GROα, GROβ, GROγ, or NAP-2 themselves, or by with IL-8, GROα, GROβ, GROγ, or NAP-2 causing another monokine to be released, such as but not limited to IL-1, IL-6 or TNF. A disease state in which, for instance, IL-1 is a major component, and whose production or action, is exacerbated or secreted in response to IL-8, would therefore be considered a disease stated mediated by IL-8.

As used herein, the term "chemokine mediated disease or disease state" refers to any and all disease states in which a chemokine which binds to an IL-8 α or b receptor plays a role, such as but not limited to with IL-8, GROα, GROβ, GROγ, or NAP-2. This would include a disease state in which, IL-8 plays a role, either by production of IL-8 itself, or by IL-8 causing another monokine to be released, such as but not limited to IL-1, IL-6 or TNF. A disease state in which, for instance, IL-1 is a major component, and whose production or action, is exacerbated or secreted in response to IL-8, would therefore be considered a disease stated mediated by IL-8.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-α) and Tumor Necrosis Factor beta (TNF-β).

As used herein, the term "chemokine" refers to any secreted polypeptide that affects the functions of cells and is a molecule which modulates interactions between cells in the immune, inflammatory or hematopoietic response, similar to the term "cytokine" above. A chemokine is primarily secreted through cell transmembranes and causes chemotaxis and activation of specific white blood cells and leukocytes, neutrophils, monocytes, macrophages, T-cells, B-cells, endothelial cells and smooth muscle cells. Examples of chemokines include, but are not limited to with IL-8, GROα, GROβ, GROγ, NAP-2, ENA-78, IP-10, MIP-1α, MIP-β, PF4, and MCP 1, 2, and 3.

In order to use a compound of Formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of Formula (I) and a pharmaceutically acceptable carrier or diluent.

Compounds of Formula (I), pharmaceutically acceptable salts thereof and pharmaceutical compositions incorporating such may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl monostearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of Formula (I) may be administered topically, that is by non-systemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the Formulation. It may however comprise as much as 10% w/w but preferably will comprise less than 5% w/w, more preferably from 0.1% to 1% w/w of the Formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation, that is by intranasal and oral inhalation administration. Appropriate dosage forms for such administration, such as an aerosol formulation or a metered dose inhaler, may be prepared by conventional techniques.

For all methods of use disclosed herein for the compounds of Formula (I), the daily oral dosage regimen will preferably be from about 0.01 to about 80 mg/kg of total body weight. The daily parenteral dosage regimen about 0.001 to about 80 mg/kg of total body weight. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

The invention will now be described by reference to the following biological examples which are merely illustrative and are not to be construed as a limitation of the scope of the present invention.

BIOLOGICAL EXAMPLES

The IL-8 cytokine-inhibiting effects of compounds of the present invention were determined by the following in vitro assay:

19

Receptor Binding Assays:

[$^{125}$I] IL-8 (human recombinant) was obtained from Amersham Corp., Arlington Heights, Ill., with specific activity 2000 Ci/mmol. Groα was obtained from NEN—New England Nuclear. All other chemicals were of analytical grade. High levels of recombinant human IL-8 type α and β receptors were individually expressed in Chinese hamster ovary cells as described previously (Holmes, et al., *Science*, 1991, 253, 1278). The Chinese hamster ovary membranes were homogenized according to a previously described protocol (Haour, et al., *J Biol Chem.*, 249 pp 2195–2205 (1974)). Except that the homogenization buffer was changed to 10 mM Tris-HCL, 1 mM MgSO4, 0.5 mM EDTA (ethylene-diaminetetra-acetic acid), 1 mMPMSF (a-toluenesulphonyl fluoride), 0.5 mg/L Leupeptin, pH 7.5. Membrane protein concentration was determined using Pierce Co. micro-assay kit using bovine serum albumin as a standard. All assays were performed in a 96-well micro plate format. Each reaction mixture contained $^{125}$I IL-8 (0.25 nM) or $^{125}$I Gro-a and 0.5 μg/mL of IL-8Ra or 1.0 μg/mL of IL-8Rb membranes in 20 mM Bis-Trispropane and 0.4 mM Tris HCl buffers, pH 8.0, containing 1.2 mM MgSO$_4$, 0.1 mM EDTA, 25 mM NaCl and 0.03% CHAPS. In addition, drug or compound of interest was added which had been pre-dissolved in DMSO so as to reach a final concentration of between 0.01 nM and 100 uM. The assay was initiated by addition of $^{125}$I-IL-8. After 1 hour at room temperature the plate was harvested using a Tomtec 96-well harvester onto a glass fiber filtermat blocked with 1% polyethylenimine/0.5% BSA and washed 3 times with 25 mM NaCl, 10 mM TrisHCl, 1 mM MgSO$_4$, 0.5 mM EDTA, 0.03% CHAPS, pH 7.4. The filter was then dried and counted on the Betaplate liquid scintillation counter. The recombinant IL-8 Ra, or Type I, receptor is also referred to herein as the non-permissive receptor and the recombinant IL-8 Rb, or Type II, receptor is referred to as the permissive receptor.

Compounds of Formula (I) as exemplified by Examples 1 to 16 all showed a positive inhibition in this assay from a range of 4 μM to about 50 μMolar.

Chemotaxis Assay:

The in vitro inhibitory properties of these compounds were determined in the neutrophil chemotaxis assay as described in Current Protocols in Immunology, Vol I, Suppl 1, Unit 6.12.3., whose disclosure is incorporated herein by reference in its entirety. Neutrophils where isolated from human blood as described in Current Protocols in Immunology Vol I, Suppl 1 Unit 7.23.1, whose disclosure is incorporated herein by reference in its entirety. The chemoattractants IL-8, GRO-α, GRO-β, GRO-γ and NAP-2 where placed in the bottom chamber of a 48 multiwell chamber (Neuro Probe, Cabin John, Md.) at a concentration between 0.1 and 100 nM. The two chambers where separated by a 5 um polycarbonate filter. When compounds of this invention were tested, they where mixed with the cells (0.001–1000 nM) just prior to the addition of the cells to the upper chamber. Incubation was allowed to proceed for between about 45 and 90 min at about 37° C. in a humidified incubator with 5% CO$_2$. At the end of the incubation period, the polycarbonate membrane was removed and the top side washed, the membrane was then stained using the Diff Quick staining protocol (Baxter Products, McGaw Park, Ill., USA). Cell which had chemotaxed to the chemokine were visually counted using a microscope. Generally, four fields where counted for each sample, these number where averaged to give the average number of cells which had migrated. Each sample was tested in triplicate and each compound repeated at least four times. To certain cells (positive control cells) no compound was added, these cells represent the maximum chemotactic response of the cells. In the case where a negative control (unstimulated) was desired, no chemokine was added to the bottom chamber. The difference between the positive control and the negative control represents the chemotactic activity of the cells.

Elastase Release Assay:

The compounds of this invention where tested for their ability to prevent Elastase release from human neutrophils. Neutrophils where isolated from human blood as described in Current Protocols in Immunology Vol I, Suppl 1 Unit 7.23.1. PMNs 0.88×10$^6$ cells suspended in Ringer's Solution (NaCl 118, KCl 4.56, NaHCO3 25, KH2PO4 1.03, Glucose 11.1, HEPES 5 mM, pH 7.4) where placed in each well of a 96 well plate in a volume of 50 ul. To this plate was added the test compound (0.001–1000 nM) in a volume of 50 ul, Cytochalasin B in a volume of 50 ul (20 ug/ml) and Ringers buffer in a volume of 50 ul. These cells where allowed to warm (37° C., 5% CO2, 95% RH) for 5 min before IL-8, GROa, GROb, GROg or NAP-2 at a final concentration of 0.01–1000 nM was added. The reaction was allowed to proceed for 45 min before the 96 well plate was centrifuged (800×g 5 min) and 100 ul of the supernatant removed. This suppernatant was added to a second 96 well plate followed by an artificial elastase substrate (MeOSuc-Ala-Ala-Pro-Val-AMC, Nova Biochem, La Jolla, Calif.) to a final concentration of 6 ug/ml dissolved in phosphate buffered saline. Immediately, the plate was placed in a fluorescent 96 well plate reader (Cytofluor 2350, Millipore, Bedford, Mass.) and data collected at 3 min intervals according to the method of Nakajima et al J. Biol Chem 254 4027 (1979). The amount of Elastase released from the PMNs was calculated by measuring the rate of MeOSuc-Ala-Ala-Pro-Val-AMC degradation.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound of the formula

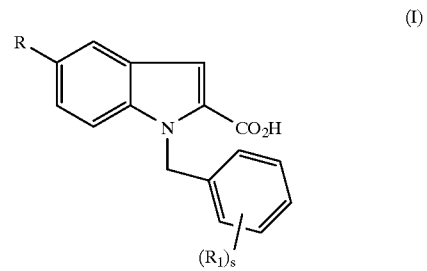

(I)

wherein

R is or X—(CH$_2$)$_n$—R$_6$;

X is oxygen or —C(O)—NH—;

$R_6$ is an optionally substituted $C_{3-7}$ cycloalkyl, optionally substituted $C_{3-7}$ cycloalkenyl, or an optionally substituted aryl;

n is 0 or an integer having a value of 1, 2, 3 or 4;

$R_1$ is hydrogen, halogen, halosubstituted $C_{1-8}$ alkyl, $C_{1-8}$ alkyl, hydroxy, $C_{1-8}$alkoxy, halosubstituted$C_{1-8}$ alkoxy, —$(CH_2)_t$aryl, O—$(CH_2)_t$ aryl, O—$CH_2$—O-$C_{1-8}$alkyl, O—$(CH_2)_v$C(O)O$C_{1-4}$alkyl, $NO_2$, $S(O)_m R_2$, $N(R_3)_2$, NHC(O)$R_4$, —C(O)$R_5$; or together two $R_1$ moieties may form a methylene dioxy ring system or together two $R_1$ moieties may form a 6 membered saturated or unsaturated ring system which may be optionally substituted;

s is an integer having a value of 1, 2, or 3;

v is an integer having a value of 1, 2, 3, or 4;

m is 0 or an integer having a value of 1 or 2;

t is 0 or an integer having a value of 1, 2, 3 or 4;

$R_2$ is an optionally substituted $C_{1-8}$ alkyl;

$R_3$ is independently hydrogen, or $C_{1-4}$ alkyl, or together with the nitrogen to which they are attached form a 5 to 7 membered saturated or unsaturated ring;

$R_4$ is independently hydrogen, or $C_{1-4}$ alkyl;

$R_5$ is hydrogen, optionally substituted $C_{1-8}$ alkyl, or $C_{1-8}$ alkoxy; provided that when $R_1$ is hydrogen, s is 1, X is O, and n=1 then $R_6$ is other than an unsubstituted phenyl; and when s=3, $R_1$ is a 4-5 methylene dioxy ring, 2-chloro, n=1, and X=O, then $R_6$ is other than a 2,6-difluoro substituted phenyl;

when s=3, $R_1$ is a 4-5 methylene dioxy ring, 2- chloro, n=1, and X=O then $R_6$ is other than a 2,- or 4- C(O)$_2$H substituted phenyl;

when s=3, $R_1$ is a 4-5 methylene dioxy ring, 2- chloro, n=1, and X=O, then $R_6$ is other than a 3-phenyloxy substituted phenyl;

or pharmaceutically acceptable salts thereof.

2. A compound according to claim 1 wherein X is oxygen.

3. A compound according to claim 2 wherein $R_6$ is an optionally substituted aryl ring.

4. A compound according to claim 3 wherein the aryl ring is substituted one or more times independently by halogen, hydroxy, hydroxy substituted $C_{1-10}$alkyl, $C_{1-10}$ alkyl, halosubstituted $C_{1-10}$ alkyl, $C_{1-10}$ alkoxy, optionally substituted $C_{1-10}$alkoxy, aryloxy, C(O)$_2$H, S-$C_{1-10}$ alkyl, N(R_3)_2, N(R_3)-C(O)$C_{1-10}$alkyl, C(O)$C_{1-10}$alkyl, cyano, nitro, a methylene dioxy ring; an optionally substituted aryl, or an optionally substituted arylalkyl.

5. The compound according to claim 1 wherein $R_1$ is hydrogen, halogen, halosubstituted $C_{1-8}$ alkyl, $C_{1-8}$ alkyl, hydroxy, $C_{1-8}$alkoxy, halosubstituted$C_{1-8}$ alkoxy, —(CH_2)_t aryl, O—(CH_2)_t aryl, NO_2, or together two $R_1$ moieties may form a methylene dioxy ring system.

6. The compound according to claim 5 wherein $R_1$ is hydrogen, 2-methoxy, 5-nitro, 4-methyl, 3,5-di-methoxy, 4-benzyloxy, 4-methoxy, 2-chloro-4,5-methylenedioxy, or 4-OCF$_3$.

7. A compound according to claim 1 wherein the compound, or its pharmaceutically acceptable salt is:

1-(2-chloro-4,5-methylenedioxybenzyl)-5-(4-methoxybenzyloxy)indole-2-carboxylic acid;

1-(2-chloro-4,5-methylenedioxybenzyl)-5-(4-trifluoromethylbenzyloxy)indole-2-carboxylic acid;

5-benzyloxy-1-(2-chloro-4,5-methylenedioxybenzyl) indole-2-carboxylic acid;

1-(2-chloro-4,5-methylenedioxybenzyl)-5-(3-trifluoromethylbenzyloxy)indole-2-carboxylic acid;

1-(2-chloro-4,5-methylenedioxybenzyl)-5-[(R)-1-phenylethoxy]indole-2-carboxylic acid;

1-(2-chloro-4,5-methylenedioxybenzyl)-5-(2-trifluoromethylbenzyloxy)indole-2-carboxylic acid;

1-(2-chloro-4,5-methylenedioxybenzyl)-5-(2-methoxybenzyloxy)indole-2-carboxylic acid;

1-(2-chloro-4,5-methylenedioxybenzyl)-5-(2,6-dichlorobenzyloxy)indole-2-carboxylic acid;

1-(2-chloro-4,5-methylenedioxybenzyl)-5-[(S)-1-phenylethoxy]indole-2-carboxylic acid;

1-(2-chloro-4,5-methylenedioxybenzyl)-5-(4-carboxybenzyloxy)indole-2-carboxylic acid;

1-(2-chloro-4,5-methylenedioxybenzyl)-5-(3-methoxybenzyloxy)indole-2-carbokylic acid;

1-(2-chloro-4,5-methylenedioxybenzyl)-5-cyclohexylmethoxyindole-2-carboxylic acid;

1-(2-chloro-4,5-methylenedioxybenzyl)-5-(3-carboxybenzyloxy)indole-2-carboxylic acid;

1-(2-chloro-4,5-methylenedioxybenzyl)-5-[4-(1H)-tetrazolylbenzyloxy]indole-2-carboxylic acid;

1-(2-chloro-4,5-methylenedioxybenzyl)-5-(N-phenylcarboxamido)indole-2-carboxylic acid;

1-(2-chloro-4,5-methylenedioxybenzyl)-5-(2-phenoxybenzyloxy)indole-2-carboxylic acid.

8. A pharmaceutical composition which comprises an effective amount of a compound according to any of claims 1 to 7 and a pharmaceutically acceptable carrier or diluent.

9. A method of treating a chemokine mediated disease state, wherein the chemokine binds to an IL-8 α or β receptor in a mammal, which comprises administering to said mammal an effective amount of a compound of according to claim 1.

10. The method according to claim 9 wherein the chemokine is IL-8.

11. The method according to claim 9 wherein the mammal is afflicted with an Il-8 mediated disease selected from psoriasis, atopic dermatitis, arthritis, asthma, chronic obstructive pulmonary disease, adult respiratory distress syndrome, inflammatory bowel disease, Crohn's disease, ulcerative colitis, stroke, septic shock, endotoxic shock, gram negative sepsis, toxic shock syndrome, cardia and renal reperfusion injury, glomerulonephritis, thrombosis, graft vs. host reaction, allograft rejections, and malaria.

12. A method of treating inflammation in a mammal in need thereof, which comprises administering to said mammal an effective amount of a compound of Formula (I) according to claim 1.

13. A method of treating asthma in a mammal in need thereof, which comprises administering to said mammal an effective amount of a compound of Formula (I) according to claim 1.

* * * * *